(12) United States Patent
Maubru et al.

(10) Patent No.: US 6,780,203 B1
(45) Date of Patent: Aug. 24, 2004

(54) DYEING COMPOSITION FOR KERATIN FIBRES

(75) Inventors: Mireille Maubru, Chatou (FR); Marie-Pascale Audousset, Asnières (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/486,558

(22) PCT Filed: Jul. 20, 1998

(86) PCT No.: PCT/FR98/01591

§ 371 (c)(1),
(2), (4) Date: Apr. 13, 2000

(87) PCT Pub. No.: WO99/11231

PCT Pub. Date: Mar. 11, 1999

(30) Foreign Application Priority Data

Sep. 1, 1997 (FR) .......................................... 97 10857

(51) Int. Cl.$^7$ .................................................. A61K 7/13
(52) U.S. Cl. .................................. 8/409; 8/421; 8/423
(58) Field of Search ............................. 8/409, 421, 423

(56) References Cited

U.S. PATENT DOCUMENTS

| | | | | |
|---|---|---|---|---|
| 3,918,896 A | * | 11/1975 | Kalopissis et al. ............. | 8/408 |
| 4,823,985 A | | 4/1989 | Grollier et al. ................ | 222/1 |
| 4,838,894 A | * | 6/1989 | Kijek et al. .................... | 8/421 |
| 5,061,289 A | | 10/1991 | Clausen et al. ................ | 8/405 |
| 5,430,159 A | | 7/1995 | Neunhoeffer et al. ......... | 8/416 |
| 5,534,267 A | | 7/1996 | Neunhoeffer et al. ......... | 8/409 |
| 5,645,610 A | * | 7/1997 | Balzer et al. .................. | 8/411 |
| 5,663,366 A | | 9/1997 | Neunhoeffer et al. ..... | 548/371.4 |
| 5,766,576 A | | 6/1998 | Löwe et al. ................... | 424/62 |
| 5,769,903 A | | 6/1998 | Audousset et al. ............ | 8/409 |
| 6,090,162 A | * | 7/2000 | Maubru ......................... | 8/421 |

FOREIGN PATENT DOCUMENTS

| | | |
|---|---|---|
| DE | 38 43 892 | 6/1990 |
| DE | 42 34 885 | 4/1994 |
| DE | 42 34 886 | 4/1994 |
| DE | 42 34 887 | 4/1994 |
| DE | 195 43 988 | 5/1997 |
| EP | 0 728 466 | 8/1996 |
| EP | 0 740 931 | 11/1996 |
| FR | 2 586 913 | 3/1987 |
| FR | 2 733 749 | 11/1996 |
| WO | 99/31054 | * 6/1999 |

OTHER PUBLICATIONS

English language translation of EP 39,030, Henkel, pp. 1–13, Nov. 1981.*
English language Derwent Abstract of EP 0 740 931, Nov. 1996.
English language abstract of FR 2 733 749, Nov. 1996.

* cited by examiner

*Primary Examiner*—Margaret Einsmann
(74) *Attorney, Agent, or Firm*—Finnegan, Henderson, Farabow, Garrett & Dunner, L.L.P.

(57) ABSTRACT

The present invention relates to a composition for the oxidation dyeing of keratin fibers, in particular human keratin fibers, such as the hair, having at least one oxidation base chosen from diaminopyrazoles and triaminopyrazoles, in combination with at least one meta-aminophenol which is halogenated ortho to the phenol, as coupler, and to the dyeing process using this composition with an oxidizing agent.

55 Claims, No Drawings

DYEING COMPOSITION FOR KERATIN FIBRES

The present invention relates to a composition for the oxidation dyeing of keratin fibres, in particular human keratin fibres such as the hair, comprising at least one oxidation base chosen from diaminopyrazoles and triaminopyrazoles, in combination with at least one meta-aminophenol which is halogenated ortho to the phenol, as coupler, and to the dyeing process using this composition with an oxidizing agent.

It is known practice to dye keratin fibres, and in particular human hair, with dye compositions containing oxidation dye precursors, in particular ortho- or para-phenylenediamines, ortho- or para-aminophenols or heterocyclic compounds such as pyrazole derivatives, which are generally referred to as oxidation bases. Oxidation dye precursors, or oxidation bases, are colourless or weakly coloured compounds which, when combined with oxidizing products, can give rise to coloured compounds and dyes by means of a process of oxidative condensation.

It is also known that the shades obtained with oxidation bases can be varied by combining them with suitably selected couplers or coloration modifiers, the latter possibly being chosen in particular from aromatic meta-diamines, meta-aminophenols, meta-diphenols and certain heterocyclic compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks, it must allow shades to be obtained in the desired intensity and it must satisfactorily withstand external agents (light, bad weather, washing, permanent-waving, perspiration or rubbing).

The dyes must also be able to cover white hair, and, lastly, they must be as unselective as possible, i.e. they must allow only the smallest possible differences in colour along the same keratin fibre, which may in fact be differently sensitized (i.e. damaged) between its tip and its root.

Compositions for the oxidation dyeing of keratin fibres, containing pyrazole derivatives such as 4,5-diaminopyrazoles, 3,4-diaminopyrazoles or 3,4,5-triaminopyrazoles as oxidation base, in combination with couplers conventionally used for oxidation dyeing, such as, for example, meta-phenylenediamines, meta-aminophenols, meta-diphenols and heterocyclic couplers such as, for example, indole derivatives, have already been proposed, in particular in German patent applications DE 3 843 892, DE 4 234 887, DE 4 234 886, DE 4 234 885 and DE 195 43 988. However, such compositions are not entirely satisfactory, in particular as regards the fastness of the colorations obtained with regard to the various attacking factors to which the hair may be subjected, and in particular with regard to perspiration.

However, the Applicant has now discovered that it is possible to obtain novel powerful dyes that are particularly resistant to the various attacking factors to which the hair may be subjected, by combining, as oxidation base, at least one diaminopyrazole and/or at least one triaminopyrazole and, as coupler, a meta-aminophenol halogenated in a position ortho to the phenol.

This discovery forms the basis of the present invention.

A first subject of the invention is thus a composition for the oxidation dyeing of keratin fibres and in particular human keratin fibres such as the hair, characterized in that it comprises, in a medium which is suitable for dyeing:
- at least one oxidation base chosen from diaminopyrazoles and triaminopyrazoles;
- and at least one coupler chosen from the halogenated meta-aminophenols of formula (I) below, and the addition salts thereof with an acid:

(I)

in which:
$R_1$ and $R_2$, which may be identical or different, represent a hydrogen atom, a halogen atom such as chlorine, bromine, iodine or fluorine, a $C_1$–$C_4$ alkyl radical, a $C_1$–$C_4$ monohydroxyalkyl radical, a $C_2$–$C_4$ polyhydroxyalkyl radical, a $C_1$–$C_4$ alkoxy radical, a $C_1$–$C_4$ monohydroxyalkoxy radical or a $C_2$–$C_4$ polyhydroxyalkoxy radical;

$R_3$ and $R_4$, which may be identical or different, represent a hydrogen atom, a $C_1$–$C_4$ alkyl radical, a $C_1$–$C_4$ monohydroxyalkyl radical, a $C_2$–$C_4$ polyhydroxyalkyl radical or a $C_1$–$C_4$ monoaminoalkyl radical; it being understood that at least one of the radicals $R_1$ and $R_2$ represents a halogen atom.

The oxidation dye composition in accordance with the invention makes it possible to obtain intense colorations in varied shades, which are relatively unselective and which have excellent properties of resistance both with respect to atmospheric agents such as light and bad weather, and with respect to perspiration and the various treatments to which the hair may be subjected (shampooing, permanent-waving). These properties are particularly noteworthy especially as regards the resistance of the colorations with respect to perspiration.

Among the $C_1$–$C_4$ alkyl and $C_1$–$C_4$ alkoxy radicals of the compounds of formula (I) above, mention may be made in particular of the methyl, ethyl, propyl, methoxy and ethoxy radicals.

Among the halogenated meta-aminophenols of formula (I), mention may be made more particularly of 3-amino-6-chlorophenol, 3-amino-6-bromophenol, 3-(β-aminoethyl)amino-6-chlorophenol, 3-(β-hydroxyethyl)-amino-6-chlorophenol and 3-amino-2-chloro-6-methylphenol, and the addition salts thereof with an acid.

Among the diaminopyrazoles which can be used as oxidation bases in the dye compositions in accordance with the invention, mention may be made more particularly of:
a) the diaminopyrazoles of formula (II) below, and the addition salts thereof with an acid:

(II)

in which:
$R_5$ represents a hydrogen atom, a $C_1$–$C_6$ alkyl radical, a $C_2$–$C_4$ hydroxyalkyl radical, a benzyl radical, a phenyl radical, a benzyl radical substituted with a halogen atom or with a $C_1$–$C_4$ alkyl or $C_1$–$C_4$ alkoxy group, or forms, with the nitrogen atom of the group $NR_7R_8$ in position 5, a hexahydropyridazine or tetrahydropyrazole heterocycle which is optionally monosubstituted with a $C_1$–$C_4$ alkyl group;

$R_6$ and $R_7$ which may be identical or different, represent a hydrogen atom, a $C_1$–$C_4$ alkyl radical, a $C_2$–$C_4$ hydroxyalkyl radical, a benzyliradical or a phenyl radical;

$R_8$ represents a hydrogen atom, or a $C_1$–$C_6$ alkyl or $C_2$–$C_4$ hydroxyalkyl radical; with the proviso that $R_6$ represents a hydrogen atom when $R_5$ represents a substituted benzyl radical or forms a heterocycle with the nitrogen atom of the group $NR_7R_8$ in position 5;

b) the diaminopyrazoles of formula (III) below, and the addition salts thereof with an acid:

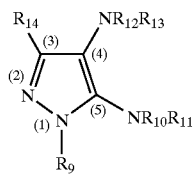
(III)

in which:

$R_9$, $R_{10}$, $R_{11}$, $R_{12}$ and $R_{13}$, which may be identical or different, represent a hydrogen atom; a linear or branched $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical

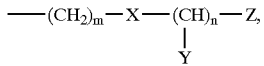

in which m and n are integers, which may be identical or different, between 1 and 3 inclusive, X represents an oxygen atom or an NH group, Y represents a hydrogen atom or a methyl radical, and Z represents a methyl radical, a group OR or NRR' in which R and R', which may be identical or different, denote a hydrogen atom, a methyl radical or an ethyl radical, it being understood that when $R_{10}$ represents a hydrogen atom, then $R_{11}$ can also represent an amino or $C_1$–$C_4$ alkylamino radical, $R_{14}$ represents a linear or branched $C_1$–$C_6$ alkyl radical; a $C_1$–$C_4$ hydroxyalkyl radical; a $C_1$–$C_4$ aminoalkyl radical; a ($C_1$–$C_4$)alkylamino($C_1$–$C_4$)alkyl radical; a di($C_1$–$C_4$)alkylamino($C_1$–$C_4$)alkyl radical; a hydroxy($C_1$–$C_4$)alkylamino($C_1$–$C_4$)alkyl radical; a ($C_1$–$C_4$) alkoxymethyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle chosen from thiophene, furan and pyridine, or alternatively a radical —$(CH_2)_p$—O—$(CH_2)_q$—OR'', in which p and q are integers, which may be identical or different, between 1 and 3 inclusive, and R'' represents a hydrogen atom or a methyl radical, it being understood that, in formula (III) above, at least one of the radicals $R_{10}$, $R_{11}$, $R_{12}$ and $R_{13}$ represents a hydrogen atom, when $R_{10}$, or $R_{12}$, respectively, represents a substituted or unsubstituted phenyl radical, or a benzyl radical or a radical

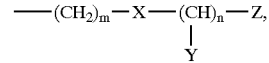

then $R_{11}$, or $R_{13}$, respectively, cannot represent any of these three radicals, when $R_{12}$ and $R_{13}$ simultaneously represent a hydrogen atom, then $R_9$ can form, with $R_{10}$ and $R_{11}$, a hexahydropyrimidine or tetrahydroimidazole heterocycle which is optionally substituted with a $C_1$–$C_4$ alkyl or 1,2,4-tetrazole radical, when $R_{10}$, $R_{11}$, $R_{12}$ and $R_{13}$ represent a hydrogen atom or a $C_1$–$C_6$ alkyl radical, then $R_9$ or $R_{14}$ can also represent a 2-, 3- or 4-pyridyl, 2- or 3-thienyl or 2- or 3-furyl heterocyclic residue which is optionally substituted with a methyl radical or alternatively a cyclohexyl radical.

Among the triaminopyrazoles which can be used as oxidation bases in the dye compositions in accordance with the invention, mention may be made more particularly of the compounds of formula (IV) below, and the addition salts thereof with an acid:

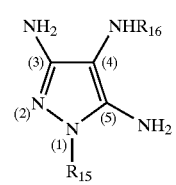
(IV)

in which:

$R_{15}$ and $R_{16}$, which may be identical or different, represent a hydrogen atom or a $C_1$–$C_4$ alkyl or $C_2$–$C_4$ hydroxyalkyl radical.

Among the diaminopyrazoles of formula (II) above, mention may be made more particularly of 4,5-diamino-1-(4'-methoxybenzyl)pyrazole, 4,5-diamino-1-(4'-methylbenzyl) pyrazole, 4,5-diamino-1-(4'-chlorobenzyl)pyrazole, 4,5-diamino-1-(3'-methoxybenzyl)pyrazole, 4-amino-1-(4'-methoxybenzyl)-5-methylaminopyrazole, 4-amino-5-(β-hydroxyethyl)amino-1-(4'-methoxybenzyl)pyrazole, 4-amino-5-(β-hydroxyethyl)amino-1-methylpyrazole, 4-amino-(3)5-methylaminopyrazole, 3-(5)4-diaminopyrazole, 4,5-diamino-1-methylpyrazole, 4,5-diamino-1-benzylpyrazole, 3-amino-4,5,7,8-tetrahydropyrazolo[1,5-a]pyrimidine, 7-amino-2,3-dihydro-1H-imidazolo[1,2-b]pyrazole and 3-amino-8-methyl-4,5,7, 8-tetrahydropyrazolo[1,5-a]pyrimidine, and the addition salts thereof with an acid.

The diaminopyrazoles of formula (III) are known compounds which can be prepared according to the synthetic process as described, for example, in French patent application FR-A-2 733 749.

Among the diaminopyrazoles of formula (III) above, mention may be made more particularly of:

1-benzyl-4,5-diamino-3-methylpyrazole, 4,5-diamino-1-(β-hydroxyethyl)-3-(4'-methoxyphenyl)-pyrazole, 4,5-diamino-1-(β-hydroxyethyl)-3-(4'-methylphenyl)-pyrazole,
4,5-diamino-1-(β-hydroxyethyl)-3-(3'-methylphenyl)-pyrazole,
4,5-diamino-3-methyl-1-isopropylpyrazole,
4,5-diamino-3-(4'-methoxyphenyl)-1-isopropylpyrazole,
4,5-diamino-1-ethyl-3-methylpyrazole,
4,5-diamino-1-ethyl-3-(4'-methoxyphenyl)pyrazole,
4,5-diamino-3-hydroxymethyl-1-methylpyrazole,
4,5-diamino-1-ethyl-3-hydroxymethylpyrazole,
4,5-diamino-3-hydroxymethyl-1-isopropylpyrazole,
4,5-diamino-3-hydroxymethyl-1-tert-butylpyrazole,
4,5-diamino-3-hydroxymethyl-1-phenylpyrazole,
4,5-diamino-3-hydroxymethyl-1-(2'-methoxyphenyl)-pyrazole,
4,5-diamino-3-hydroxymethyl-1-(3'-methoxyphenyl)-pyrazole,
4,5-diamino-3-hydroxymethyl-1-(4'-methoxyphenyl)-pyrazole,
1-benzyl-4,5-diamino-3-hydroxymethylpyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-ethylpyrazole,
4,5-diamino-3-dimethylaminomethyl-1-isopropylpyrazole,
4,5-diamino-3-dimethylaminomethyl-1-tert-butylpyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethylpyrazole,
4,5-diamino-3-[(β-hydroxyethyl)aminomethyl]-1-methylpyrazole,
4,5-diamino-3-[(β-hydroxyethyl)aminomethyl]-1-isopropylpyrazole,
4,5-diamino-1-ethyl-3-[(β-hydroxyethyl)aminomethyl]-pyrazole,
1-tert-butyl-4,5-diamino-3-[(β-hydroxyethyl)-aminomethyl]pyrazole,
4-amino-5-(β-hydroxyethyl)amino-1,3-dimethylpyrazole,
4-amino-5-(β-hydroxyethyl)amino-1-isopropyl-3-methylpyrazole,
4-amino-5-(β-hydroxyethyl)amino-1-ethyl-3-methylpyrazole,
4-amino-5-(β-hydroxyethyl)amino-1-tert-butyl-3-methylpyrazole,
4-amino-5-(β-hydroxyethyl)amino-1-phenyl-3-methylpyrazole,
4-amino-5-(β-hydroxyethyl)amino-1-(2-methoxyphenyl)-3-methylpyrazole,
4-amino-5-(β-hydroxyethyl)amino-1-(3-methoxyphenyl)-3-methylpyrazole,
4-amino-5-(β-hydroxyethyl)amino-1-(4-methoxyphenyl)-3-methylpyrazole,
4-amino-5-(β-hydroxyethyl)amino-1-benzyl-3-methylpyrazole,
4-amino-1-ethyl-3-methyl-5-methylaminopyrazole,
4-amino-1-tert-butyl-3-methyl-5-methylaminopyrazole,
4,5-diamino-1,3-dimethylpyrazole,
4,5-diamino-3-tert-butyl-1-methylpyrazole,
4,5-diamino-1-tert-butyl-3-methylpyrazole,
4,5-diamino-1-methyl-3-phenylpyrazole,
4,5-diamino-1-(β-hydroxyethyl)-3-methylpyrazole,
4,5-diamino-1-(β-hydroxyethyl)-3-phenylpyrazole,
4,5-diamino-1-methyl-3-(2'-chlorophenyl)pyrazole,
4,5-diamino-1-methyl-3-(4'-chlorophenyl)pyrazole,
4,5-diamino-1-methyl-3-(3'-trifluoromethylphenyl)-pyrazole,
4,5-diamino-1,3-diphenylpyrazole,
4,5-diamino-3-methyl-1-phenylpyrazole,
4-amino-1,3-dimethyl-5-phenylaminopyrazole,
4-amino-1-ethyl-3-methyl-5-phenylaminopyrazole,
4-amino-1,3-dimethyl-5-methylaminopyrazole,
4-amino-3-methyl-1-isopropyl-5-methylaminopyrazole,
4-amino-3-isobutoxymethyl-1-methyl-5-methylaminopyrazole,
4-amino-3-methoxyethoxymethyl-1-methyl-5-methylaminopyrazole,
4-amino-3-hydroxymethyl-1-methyl-5-methylaminopyrazole,
4-amino-1,3-diphenyl-5-phenylaminopyrazole,
4-amino-3-methyl-5-methylamino-1-phenylpyrazole,
4-amino-1,3-dimethyl-5-hydrazinopyrazole,
5-amino-3-methyl-4-methylamino-1-phenylpyrazole,
5-amino-1-methyl-4-(N,N-methylphenyl)amino-3-(4'-chlorophenyl)pyrazole,
5-amino-3-ethyl-1-methyl-4-(N,N-methylphenyl)aminopyrazole,
5-amino-1-methyl-4-(N,N-methylphenyl)amino-3-phenylpyrazole,
5-amino-3-ethyl-4-(N,N-methylphenyl)aminopyrazole,
5-amino-4-(N,N-methylphenyl)amino-3-phenylpyrazole,
5-amino-4-(N,N-methylphenyl)amino-3-(4'-methylphenyl)pyrazole,
5-amino-3-(4'-chlorophenyl)-4-(N,N-methylphenyl)-aminopyrazole,
5-amino-3-(4'-methoxyphenyl)-4-(N,N-methylphenyl)-aminopyrazole,
4-amino-5-methylamino-3-phenylpyrazole,
4-amino-5-ethylamino-3-phenylpyrazole,
4-amino-5-ethylamino-3-(4'-methylphenyl)pyrazole,
4-amino-3-phenyl-5-propylaminopyrazole,
4-amino-5-butylamino-3-phenylpyrazole,
4-amino-3-phenyl-5-phenylaminopyrazole,
4-amino-5-benzylamino-3-phenylpyrazole,
4-amino-5-(4'-chlorophenyl)amino-3-phenylpyrazole,
4-amino-3-(4'-chlorophenyl)-5-phenylaminopyrazole, 4-amino-3-(4'-methoxyphenyl)-5-phenylaminopyrazole,
1-(4'-chlorobenzyl)-4,5-diamino-3-methylpyrazole,
4,5-diamino-3-hydroxymethyl-1-isopropylpyrazole,
4-amino-1-ethyl-3-methyl-5-methylaminopyrazole,
4-amino-5-(2'-aminoethyl)amino-1,3-dimethylpyrazole,
and the addition salts thereof with an acid.

Among these diaminopyrazoles of formula (III) above, the ones more particularly preferred are:
4,5-diamino-1,3-dimethylpyrazole,
4,5-diamino-3-methyl-1-phenylpyrazole,
4,5-diamino-1-methyl-3-phenylpyrazole,
4-amino-1,3-dimethyl-5-hydrazinopyrazole,
1-benzyl-4,5-diamino-3-methylpyrazole,
4,5-diamino-3-tert-butyl-1-methylpyrazole,
4,5-diamino-1-tert-butyl-3-methylpyrazole,
4,5-diamino-1-(β-hydroxyethyl)-3-methylpyrazole,
4,5-diamino-1-ethyl-3-methylpyrazole,
4,5-diamino-1-ethyl-3-(4'-methoxyphenyl)pyrazole,
4,5-diamino-1-ethyl-3-hydroxymethylpyrazole,
4,5-diamino-3-hydroxymethyl-1-methylpyrazole,
4,5-diamino-3-hydroxymethyl-1-isopropylpyrazole,
4,5-diamino-3-methyl-1-isopropylpyrazole,
4-amino-5-(2'-aminoethyl)amino-1,3-dimethylpyrazole,
and the addition salts thereof with an acid.

Among the triaminopyrazoles of formula (IV) above, mention may be made more particularly of 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The diaminopyrazole(s) and/or the triaminopyrazole(s) in accordance with the invention and/or the corresponding addition salt(s) with an acid preferably represent(s) from 0.0005 to 12% by weight approximately relative to the total weight of the dye composition, and even more preferably from 0.005 to 6% by weight approximately relative to this weight.

The halogenated meta-aminophenol(s) of formula (I) in accordance with the invention and/or the corresponding addition salt(s) with an acid preferably represent(s) from 0.0001 to 5% by weight approximately relative to the total weight of the dye composition, and even more preferably from 0.005 to 3% by weight approximately relative to this weight.

The dye compositions in accordance with the invention can contain other couplers conventionally used for oxidation dyeing, other than the halogenated meta-aminophenols of formula (I), and/or other oxidation bases conventionally used for oxidation dyeing, other than a diaminopyrazole and a triaminopyrazole and/or direct dyes, in particular in order to modify the shades or to enrich them with glints.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) generally consists of water or of a mixture of water and at least one organic solvent to dissolve the compounds which would not be sufficiently soluble in water. Organic solvents which may be mentioned, for example, are $C_1-C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately and even more preferably between 5 and 11 approximately. It can be adjusted to the desired value by means of acidifying or basifying agents usually used in the dyeing of keratin fibres.

Among the acidifying agents which may be mentioned, for example, are inorganic or organic acids such as hydrochloric acid, orthophosphoric acid, carboxylic acids such as tartaric acid, citric acid and lactic acid, and sulphonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (V) below:

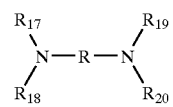

(V)

in which R is a propylene residue optionally substituted with a hydroxyl group or a $C_1-C_4$ alkyl radical; $R_{17}$, $R_{18}$, $R_{19}$ and $R_{20}$, which may be identical or different, represent a hydrogen atom or a $C_1-C_4$ alkyl or $C_1-C_4$ hydroxyalkyl radical.

The dye composition according to the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetrating agents, sequestering agents, fragrances, buffers, dispersants, conditioners such as, for example, volatile or non-volatile, modified or unmodified silicones, film-forming agents, ceramides, preserving agents and opacifiers.

Needless to say, a person skilled in the art will take care to select this or these optional additional compound(s) such that the advantageous properties intrinsically associated with the combination in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

A subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH with the aid of an oxidizing agent which is added to the dye composition just at the time of use, or which is present in an oxidizing composition that is applied simultaneously or sequentially.

According to one particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left to stand on them for 3 to 60 minutes approximately, preferably 5 to 40 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates, persalts such as perborates, percarbonates and persulphates, and peracids. Hydrogen peroxide is particularly preferred.

The pH of the oxidizing composition containing the oxidizing agent as defined above is such that after mixing with the dye composition, the pH of the resulting composition applied to the keratin fibres preferably ranges between 3 and 12 approximately and even more preferably between 5 and 11. It is adjusted to the desired value by means of acidifying or basifying agents usually used in the dyeing of keratin fibres and as defined above.

The oxidizing composition as defined above can also contain various adjuvants conventionally used in compositions for dyeing the hair and as defined above.

The composition which is finally applied to the keratin-fibres can be in various forms, such as in the form of liquids, creams or gels or in any other form which is suitable for dyeing keratin fibres, and in particular human hair.

Another subject of the invention is a multi-compartment dyeing device or "kit" or any other multi-compartment packaging system, a first compartment of which contains the dye composition as defined above, and a second compartment of which contains the oxidizing composition as defined above. These devices can be equipped with a means for applying the desired mixture to the hair, such as the devices described in patent FR-2 586 913 in the name of the Applicant.

The examples which follow are intended to illustrate the invention without, however, limiting its scope.

EXAMPLES

Comparative Dyeing Examples 1 to 4

The dye compositions below, in accordance with the invention, were prepared (contents in grams):

| EXAMPLE | 1(*) | 2 | 3 | 4 |
|---|---|---|---|---|
| 4,5-diamino-1-ethyl-3-methylpyrazole dihydrochloride (oxidation base) | 0.639 | 0.639 | 0.639 | 0.639 |
| 3-aminophenol (coupler not forming part of the invention) | 0.327 | — | — | — |
| 3-amino-6-chlorophenol (coupler in accordance with the invention) | — | 0.431 | — | — |
| 3-(β-aminoethyl)amino-6-chlorophenol (coupler in accordance with the invention) | — | — | 0.560 | — |
| 3-(β-hydroxyethyl)amino-6-chlorophenol (coupler in accordance with the invention) | — | — | — | 0.563 |
| Common dye support | () | () | () | () |
| Demineralized water qs | 100 g | 100 g | 100 g | 100 g |

(*):example not forming part of the invention
(**) common dye support:

| | |
|---|---|
| -Oleyl alcohol polyglycerated with 2 mol of glycerol | 4.0 g |
| -Oleyl alcohol polyglycerated with 4 mol of glycerol, containing 78% active material (A.M.) | 5.69 g A.M. |
| -Oleic aid | 3.0 g |
| -Oleylamine containing 2 mol of ethylene oxide, sold under the tradename Ethomeen O12 ® by the company Akzo | 7.0 g |
| -Diethylaminopropyl laurylamino succinamate, sodium salt, containing 55% A.M. | 3.0 g A.M. |
| -Oleyl alcohol | 5.0 g |
| -Oleic acid diethanolamide | 12.0 g |
| -Propylene glycol | 3.5 g |
| -Ethyl alcohol | 7.0 g |
| -Dipropylene glycol | 0.5 g |
| -Propylene glycol monomethyl ether | 9.0 g |
| -Sodium metabisulphite as an aqueous solution containing 35% A.M. | 0.455 g A.M. |
| -Ammonium acetate | 0.8 g |
| -Antioxidant, sequestering agent | q.s. |
| -Fragrance, preserving agent | q.s. |
| -Aqueous ammonia containing 20% $NH_3$ | 10 g |

It is important to note that each of the dye compositions 1 to 4 above contains the same molar amount of coupler, i.e. $3 \times 10^{-3}$ mol.

At the time of use, each dye composition above was mixed with an equal amount by weight of an oxidizing composition consisting of a 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

The locks of dyed hair were then subjected to a test of resistance to the action of perspiration.

The colour of the locks of hair dyed with compositions 1 to 4 was evaluated in the Munsell system using a Minolta® CM 2002 calorimeter, before the test of resistance to the action of perspiration.

According to the Munsell notation, a colour is defined by the expression H V/C in which the three parameters respectively denote the shade or Hue (H), the intensity or Value (V) and the purity or Chromaticity (C), the oblique line in this expression simply being a convention and not indicating a ratio.

The locks of dyed hair were then subjected to the test of resistance to the action of perspiration.

To do this, the locks of dyed hair were immersed in a crystallizing dish covered with a watch glass and containing a solution of synthetic sweat of the following composition:

| | |
|---|---|
| - NaCl | 1.0 g |
| - Potassium hydrogen phosphate | 0.1 g |
| - Histidine | 0.025 g |
| - Lactic acid qs | pH 3.2 |
| - Distilled water qs | 100 g |

The locks of dyed hair were left to stand in this synthetic sweat solution for 48 hours at 37° C. The locks were then rinsed, followed by drying.

The colour of the locks was then re-evaluated in the Munsell system using a Minolta® CM 2002 colorimeter.

The difference between the colour of the lock before the test of resistance to perspiration and the colour of the lock after the test of resistance to perspiration was calculated by applying the Nickerson formula $$\Delta E = 0.4 C_0 dH + 6dV + 3dC$$

as described, for example, in "Couleur, Industrie et Technique [Colour, Industry and Technique]"; pages 14–17; vol. No 5; 1978.

In this formula, $\Delta E$ represents the difference in colour between two locks, $\Delta H$, $\Delta V$ and $\Delta C$ represent the variation in absolute value of the parameters H, V and C, and $C_0$ represents the purity of the lock relative to which it is desired to evaluate the colour difference.

The degradation of the colour is proportionately greater the larger the value of $\Delta E$.

The results are given in the table below:

| EXAMPLE | Colour of the hair before the test | Colour of the hair after the test | Degradation of the colour | | | |
|---|---|---|---|---|---|---|
| | | | $\Delta H$ | $\Delta V$ | $\Delta C$ | $\Delta E$ |
| 1(*) | 9.2 RP 3/3/2.6 | 2.5 YR 3.9/2.1 | 13.3 | 0.6 | 0.5 | 18.9 |
| 2 | 2.6 RP 3.0/3.7 | 6.1 RP 3.5/3.2 | 3.5 | 0.5 | 0.5 | 9.7 |
| 3 | 2.6 RP 3.0/2.9 | 4.1 RP 3.0/2.9 | 1.5 | 0 | 0 | 1.7 |
| 4 | 2.7 RP 3.2/3.2 | 6.1 RP 3.5/3.0 | 3.4 | 0.3 | 0.2 | 6.8 |

These results show that the coloration obtained using the dye composition of Example 1 not forming part of the invention, since it contains a combination of a diaminopyrazole and a non-halogenated meta-aminophenol, is markedly less resistant to the action of perspiration than the colorations obtained using the compositions of Examples 2 to 4, all of which form part of the invention since they contain a combination of a diaminopyrazole and a meta-aminophenol which is halogenated ortho to the phenol.

Dyeing Examples 5 to 8

The dye compositions below, in accordance with the invention, were prepared (contents in grams):

| EXAMPLE | 5 | 6 | 7 | 8 |
|---|---|---|---|---|
| 4,5-diaminopyrazole dihydrochloride (oxidation base | 0.513 | — | — | — |
| 1-methyl-4,5-diaminopyrazole dihydrochloride (oxidation base) | — | 0.555 | 0.555 | 0.555 |
| 3-amino-2-chloro-6-methylphenol (coupler in accordance with the invention) | 0.473 | 0.473 | — | — |
| 3-amino-6-chlorophenol (coupler in accordance with the invention) | — | — | 0.431 | — |
| 3-(β-aminoethyl)amino-6-chlorophenol (coupler in accordance with the invention) | — | — | — | 0.560 |
| Common dye support | () | () | () | () |
| Demineralized water qs | 100 g | 100 g | 100 g | 100 g |

(**) common dye support:

This is identical to the one used for Examples 1 to 4 above.

At the time of use, each dye composition above was mixed with an equal amount by weight of an oxidizing composition consisting of a 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

The locks were dyed in the shades given in the table below:

| EXAMPLE | SHADE OBTAINED |
|---|---|
| 5 | Red-coppery |
| 6 | Red-coppery |
| 7 | Red-iridescent |
| 8 | Iridescent red |

What is claimed is:

1. A composition for the oxidation dyeing of human keratin fibers comprising:
   at least one oxidation base chosen from diaminopyrazoles of formula (II) and acid-addition salts thereof:

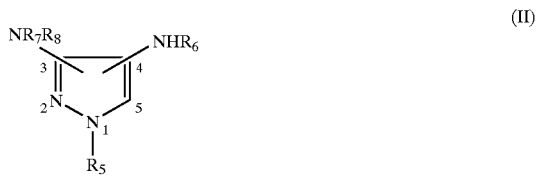

(II)

in which:
   $R_5$ is chosen from a $C_2$–$C_4$ hydroxyalkyl radical;
   $R_6$ and $R_7$, which are identical or different, are chosen from a hydrogen atom, a $C_1$–$C_4$ alkyl radical, a $C_2$–$C_4$ hydroxyalkyl radical, a benzyl radical and a phenyl radical; and
   $R_8$ is chosen from a hydrogen atom, a $C_1$–$C_6$ alkyl radical and a $C_2$–$C_4$ hydroxyalkyl radical, and
   and at least one coupler chosen from 3-amino-2-chloro-6-methylphenol and acid addition salts thereof.

2. A composition according to claim 1, wherein said composition is in a medium suitable for dyeing.

3. A composition according to claim 1, wherein said at least one oxidation base is present in an amount ranging from 0.0005 to 12% by weight relative to the total weight of the composition.

4. A composition according to claim 3, wherein said at least one oxidation base is present in an amount ranging from 0.005 to 6% by weight relative to the total weight of the composition.

5. A composition according to claim 1, wherein said at least one coupler is present in an amount ranging from 0.0001 to 5% by weight relative to the total weight of the composition.

6. A composition according to claim 5, wherein said at least one coupler is present in an amount ranging from 0.005 to 3% by weight relative to the total weight of the composition.

7. A composition according to claim 1, wherein said acid addition salts are chosen from hydrochlorides, hydrobromides, sulphates, tartrates, lactates and acetates.

8. A composition according to claim 2, wherein said medium suitable for dyeing or support comprises water or a mixture of water and at least one organic solvent.

9. A composition according to claim 8, wherein said at least one organic solvent is chosen from $C_1$–$C_4$ lower alkanols, glycerol, glycols and glycol ethers, and aromatic alcohols.

10. A composition according to claim 1, wherein said composition has a pH ranging from 3 to 12.

11. A composition according to claim 1, wherein said composition is in the form of a liquid, a cream, or a gel.

12. A composition according to claim 11, wherein said composition is in the form of a liquid, a cream, a gel, or in any other form suitable for dyeing human hair.

13. A method for dyeing keratin fibers, comprising:

(a) applying to said keratin fibers at least one dye composition, which comprises at least one oxidation base chosen from diaminopyrazoles of formula (II) and acid-addition salts thereof:

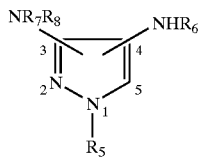

(II)

in which:

$R_5$ is chosen from a $C_2$–$C_4$ hydroxyalkyl radical;

$R_6$ and $R_7$, which are identical or different, are chosen from a hydrogen atom, a $C_1$–$C_4$ alkyl radical, a $C_2$–$C_4$ hydroxyalkyl radical, a benzyl radical and a phenyl radical; and $R_8$ is chosen from a hydrogen atom, a $C_1$–$C_6$ alkyl radical and a $C_2$–$C_4$ hydroxyalkyl radical, and at least one coupler chosen from 3-amino-2-chloro-6-methylphenol and acid addition salts thereof; and (b) developing a color at an acidic, neutral or alkaline pH with the aid of an oxidizing agent, wherein said oxidizing agent is added to said at least one dye composition at the time of application of said composition, or wherein said oxidizing agent is present in an oxidizing composition, and wherein said oxidizing composition is applied simultaneously or sequentially with said at least one dye composition.

14. A method according to claim 13, wherein said keratin fibers are human keratin fibers.

15. A method according to claim 14, wherein said human keratin fibers are human hair.

16. A method according to claim 13, wherein said oxidizing agent is chosen from hydrogen peroxide, urea peroxide, alkali metal bromates, persalts, and peracids.

17. A method according to claim 16, wherein said persalts are chosen from perborates, percarbonates and persulphates.

18. A multi-compartment kit for dyeing keratin fibers, comprising at least two compartments, wherein one compartment comprises an oxidizing composition, and another compartment comprises a composition for the oxidation dyeing of keratin fibers, said composition for the oxidation dyeing of keratin fibers comprising:

at least one oxidation base chosen from diaminopyrazoles of formula (II) and acid-addition salts thereof:

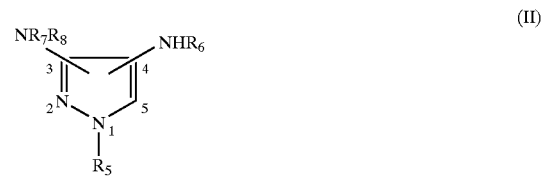

(II)

in which:

$R_5$ is chosen from a $C_2$–$C_4$ hydroxyalkyl radical;

$R_6$ and $R_7$, which are identical or different, are chosen from a hydrogen atom, a $C_1$–$C_4$ alkyl radical, a $C_2$–$C_4$ hydroxyalkyl radical, a benzyl radical and a phenyl radical; and $R_8$ is chosen from a hydrogen atom, a $C_1$–$C_6$ alkyl radical and a $C_2$–$C_4$ hydroxyalkyl radical, and at least one coupler chosen from 3-amino-2-chloro-6-methylphenol and acid addition salts thereof.

19. A multi-compartment kit for dyeing keratin fibers, comprising at least two compartments, wherein one compartment comprises an oxidizing composition, and another compartment comprises a composition for the oxidation dyeing of keratin fibers, said composition for the oxidation dyeing of keratin fibers comprising:

at least one oxidation base chosen from diaminopyrazoles, triaminopyrazoles, and acid-addition salts thereof;

and at least one coupler chosen from halogenated meta-aminophenols of formula (I), and acid addition salts thereof:

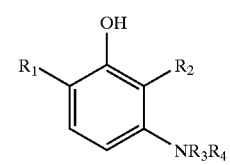

(I)

in which:

$R_1$ is chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ alkoxy radical, a $C_1$–$C_4$ monohydroxyalkoxy radical and a $C_2$–$C_4$ polyhydroxyalkoxy radical;

$R_2$ is chosen from a halogen atom; and $R_3$ and $R_4$, which are identical or different, are chosen from a hydrogen atom, a $C_1$–$C_4$ alkyl radical, a $C_1$–$C_4$ monohydroxyalkyl radical, a $C_2$–$C_4$ polyhydroxyalkyl radical and a $C_1$–$C_4$ monoaminoalkyl radical.

20. A multi-compartment kit according to claim 19, wherein $R_1$ is chosen from $R_1$ is chosen from a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ alkoxy radical, a $C_1$–$C_4$ monohydroxyalkoxy radical and a $C_2$–$C_4$ polyhydroxyalkoxy radical.

21. A multi-compartment kit according to claim 19, wherein $R_1$ is chosen from a $C_1$–$C_4$ alkyl radical.

22. A multi-compartment kit according to claim 19, wherein the at least one coupler is chosen from 3-amino-2-chloro-6-methylphenol and acid addition salts thereof.

23. A multi-compartment kit according to claim 19, wherein the at least one oxidation base is chosen from diaminopyrazoles of formula (II), and acid addition salts thereof:

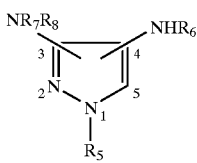

in which:

$R_5$ is chosen from a $C_2$–$C_4$ hydroxyalkyl radical;

$R_6$ and $R_7$ which are identical or different, are chosen from a hydrogen atom, a $C_1$–$C_4$ alkyl radical, a $C_2$–$C_4$ hydroxyalkyl radical, a benzyl radical and a phenyl radical; and $R_8$ is chosen from a hydrogen atom, a $C_1$–$C_6$ alkyl radical and a $C_2$–$C_4$ hydroxyalkyl radical.

24. A method for dyeing keratin fibers, comprising:

(a) applying to said keratin fibers at least one dye composition, which comprises at least one oxidation base chosen from diaminopyrazoles, triaminopyrazoles, and acid-addition salts thereof;

and at least one coupler chosen from halogenated meta-aminophenols of formula (I), and acid addition salts thereof:

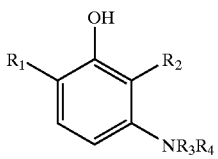

in which:

$R_1$ is chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ alkoxy radical, a $C_1$–$C_4$ monohydroxyalkoxy radical and a $C_2$–$C_4$ polyhydroxyalkoxy radical;

$R_2$ is chosen from a halogen atom; and $R_3$ and $R_4$, which are identical or different, are chosen from a hydrogen atom, a $C_1$–$C_4$ alkyl radical, a $C_1$–$C_4$ monohydroxyalkyl radical, a $C_2$–$C_4$ polyhydroxyalkyl radical and a $C_1$–$C_4$ monoaminoalkyl radical; and (b) developing a color at an acidic, neutral or alkaline pH with the aid of an oxidizing agent, wherein said oxidizing agent is added to said at least one dye composition at the time of application of said composition, or wherein said oxidizing agent is present in an oxidizing composition, and wherein said oxidizing composition is applied simultaneously or sequentially with said at least one dye composition.

25. A method according to claim 24, wherein $R_1$ is chosen from $R_1$ is chosen from a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ alkoxy radical, a $C_1$–$C_4$ monohydroxyalkoxy radical and a $C_2$–$C_4$ polyhydroxyalkoxy radical.

26. A method according to claim 24, wherein $R_1$ is chosen from a $C_1$–$C_4$ alkyl radical.

27. A method according to claim 24, wherein the at least one coupler is chosen from 3-amino-2-chloro-6-methylphenol and acid addition salts thereof.

28. A method according to claim 24, wherein the at least one oxidation base is chosen from diaminopyrazoles of formula (II), and acid addition salts thereof:

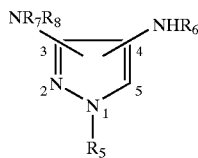

in which:

$R_5$ is chosen from a $C_2$–$C_4$ hydroxyalkyl radical;

$R_6$ and $R_7$ which are identical or different, are chosen from a hydrogen atom, a $C_1$–$C_4$ alkyl radical, a $C_2$–$C_4$ hydroxyalkyl radical, a benzyl radical and a phenyl radical; and $R_8$ is chosen from a hydrogen atom, a $C_1$–$C_6$ alkyl radical and a $C_2$–$C_4$ hydroxyalkyl radical.

29. A method according to claim 24, wherein said keratin fibers are human keratin fibers.

30. A method according to claim 29, wherein said human keratin fibers are human hair.

31. A method according to claim 24, wherein said oxidizing agent is chosen from hydrogen peroxide, urea peroxide, alkali metal bromates, persalts, and peracids.

32. A method according to claim 31, wherein said persalts are chosen from perborates, percarbonates and persulphates.

33. A composition for the oxidation dyeing of human keratin fibers comprising:

at least one oxidation base chosen from diaminopyrazoles, triaminopyrazoles, and acid-addition salts thereof, and at least one coupler chosen from halogenated meta-aminophenols of formula (I), and acid addition salts thereof:

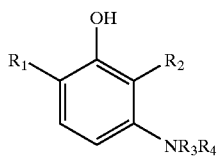

in which:

$R_1$ is chosen from a hydrogen atom, a halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ alkoxy radical, a $C_1$–$C_4$ monohydroxyalkoxy radical and a $C_2$–$C_4$ polyhydroxyalkoxy radical;

$R_2$ is chosen from a halogen atom; and $R_3$ and $R_4$, which are identical or different, are chosen from a hydrogen atom, a $C_1$–$C_4$ alkyl radical, a $C_1$–$C_4$ monohydroxyalkyl radical, a $C_2$–$C_4$ polyhydroxyalkyl radical and a $C_1$–$C_4$ monoaminoalkyl radical.

34. A composition according to claim 33, wherein said halogen atoms are chosen from chlorine, bromine, iodine and fluorine.

35. A composition according to claim 33, wherein said diaminopyrazoles are chosen from:

a) diaminopyrazoles of formula (II), and acid addition salts thereof:

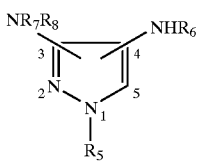

(II)

in which:
R$_5$ is chosen from a hydrogen atom, a C$_1$–C$_6$ alkyl radical, a C$_2$–C$_4$ hydroxyalkyl radical, a benzyl radical, a phenyl radical, a benzyl radical substituted with a halogen atom, a C$_1$–C$_4$ alkyl radical or C$_1$–C$_4$ alkoxy radical, or R$_5$ forms, with the nitrogen atom of the group NR$_7$R$_8$ in position 5, a hexahydropyridazine or tetrahydropyrazole heterocycle which is optionally monosubstituted with a C$_1$–C$_4$ alkyl group;

R$_6$ and R$_7$ which are identical or different, are chosen from a hydrogen atom, a C$_1$–C$_4$ alkyl radical, a C$_2$–C$_4$ hydroxyalkyl radical, a benzyl radical and a phenyl radical;

R$_8$ is chosen from a hydrogen atom, a C$_1$–C$_6$ alkyl radical and a C$_2$–C$_4$ hydroxyalkyl radical;

with the proviso that R$_6$ is a hydrogen atom when R$_5$ either is a substituted benzyl radical or forms a heterocycle with the nitrogen atom of the group NR$_7$R$_8$ in position 5; and b) diaminopyrazoles of formula (III), and acid addition salts thereof:

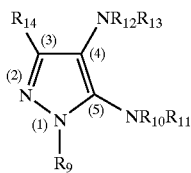

(III)

in which:
R$_9$, R$_{10}$, R$_{11}$, R$_{12}$ and R$_{13}$, which are identical or different, are chosen from a hydrogen atom; a linear or branched C$_1$–C$_6$ alkyl radical; a C$_2$–C$_4$ hydroxyalkyl radical; a C$_2$–C$_4$ aminoalkyl radical; a phenyl radical; a phenyl radical substituted with a halogen atom or a C$_1$–C$_4$ alkyl, C$_1$–C$_4$ alkoxy, nitro, trifluoromethyl, amino or C$_1$–C$_4$ alkylamino radical; a benzyl radical; a benzyl radical substituted with a halogen atom or with a C$_1$–C$_4$ alkyl, C$_1$–C$_4$ alkoxy, methylenedioxy or amino radical; and a radical

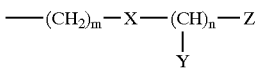

in which m and n are integers, which are identical or different, ranging from 1 to 3 inclusive, X is chosen from an oxygen atom and an NH group, Y is chosen from a hydrogen atom and a methyl radical, and Z is chosen from a methyl radical and a group OR or NRR' in which R and R', which are identical or different, are chosen from a hydrogen atom, a methyl radical and an ethyl radical, with the proviso that when R$_{10}$ is a hydrogen atom, then R$_{11}$ can also be an amino or C$_1$–C$_4$ alkylamino radical, R$_{14}$ is chosen from a linear or branched C$_1$–C$_6$ alkyl radical; a C$_1$–C$_4$ hydroxyalkyl radical; a C$_1$–C$_4$ aminoalkyl radical; a (C$_1$–C$_4$)alkylamino(C$_1$–C$_4$)alkyl radical; a di(C$_1$–C$_4$)alkylamino(C$_1$–C$_4$)alkyl radical; a hydroxy(C$_1$–C$_4$)alkylamino(C$_1$–C$_4$)alkyl radical; a (C$_1$–C$_4$)alkoxymethyl radical; a phenyl radical; a phenyl radical substituted with a halogen atom or with a C$_1$–C$_4$ alkyl, C$_1$–C$_4$ alkoxy, nitro, trifluoromethyl, amino or C$_1$–C$_4$ alkylamino radical; a benzyl radical; a benzyl radical substituted with a halogen atom or with a C$_1$–C$_4$ alkyl, C$_1$–C$_4$ alkoxy, nitro, trifluoromethyl, amino or C$_1$–C$_4$ alkylamino radical; a heterocycle chosen from thiophene, furan and pyridine; and a radical —(CH$_2$)$_p$—O—(CH$_2$)$_q$—OR", in which p and q are integers, which are identical or different, ranging from 1 to 3 inclusive, and R" is chosen from a hydrogen atom and a methyl radical;

with the provisos that, in formula (III),
at least one of the radicals R$_{10}$, R$_{11}$, R$_{12}$ and R$_{13}$ is a hydrogen atom;

when R$_{10}$, or R$_{12}$, respectively, is a substituted or unsubstituted phenyl radical, or a benzyl radical or a radical

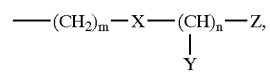

then R$_{11}$, or R$_{13}$, respectively, is not a substituted or unsubstituted phenyl radical, or a benzyl radical or a radical

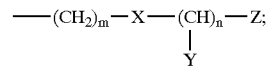

when R$_{12}$ and R$_{13}$ simultaneously represent a hydrogen atom, then R$_9$ can form, with R$_{10}$ and R$_{11}$, a hexahydropyrimidine or tetrahydroimidazole heterocycle which is optionally substituted with a C$_1$–C$_4$ alkyl or 1,2,4-tetrazole radical;

when R$_{10}$, R$_{11}$, R$_{12}$ and R$_{13}$ represent a hydrogen atom or a C$_1$–C$_6$ alkyl radical, then R$_9$ or R$_{14}$ can also represent a 2-, 3- or 4-pyridyl, 2- or 3-thienyl or 2- or 3-furyl heterocyclic residue which is optionally substituted with a methyl radical or a cyclohexyl radical.

36. A composition according to claim 35, wherein said diaminopyrazoles of formula (II) are chosen from:
4,5-diamino-1-(4'-methoxybenzyl)pyrazole,
4,5-diamino-1-(4'-methylbenzyl)pyrazole,
4,5-diamino-1-(4'-chlorobenzyl)pyrazole,
4,5-diamino-1-(3'-methoxybenzyl)pyrazole,
4-amino-1-(4'-methoxybenzyl)-5-methylaminopyrazole,
4-amino-5-(β-hydroxyethyl)amino-1-(4'-methoxybenzyl)pyrazole,
4-amino-5-(β-hydroxyethyl)amino-1-methylpyrazole,
4-amino-(3)5-methylaminopyrazole,
3-(5)4-diaminopyrazole,
4,5-diamino-1-methylpyrazole,
4,5-diamino-1-benzylpyrazole,
3-amino-4,5,7,8-tetrahydropyrazolo{1,5-a}pyrimidine,
7-amino-2,3-dihydro-1H-imidazolo{1,2-b}pyrazole,
3-amino-8-methyl-4,5,7,8-tetrahydropyrazolo{1,5-a}pyrimidine, and acid addition salts thereof.

37. A composition according to claim 35, wherein said diaminopyrazoles of formula (III) are chosen from:
1-benzyl-4,5-diamino-3-methylpyrazole,
4,5-diamino-1-(β-hydroxyethyl)-3-(4'-methoxyphenyl)pyrazole, 4,5-diamino-1-(β-hydroxyethyl)-3-(4'-methylphenyl) pyrazole,
4,5-diamino-1-(β-hydroxyethyl)-3-(3'-methylphenyl) pyrazole,
4,5-diamino-3-methyl-1-isopropylpyrazole,
4,5-diamino-3-(4'-methoxyphenyl)1-isopropylpyrazole,
4,5-diamino-1-ethyl-3-methylpyrazole,
4,5-diamino-1-ethyl-3-(4'-methoxyphenyl)pyrazole,
4,5-diamino-3-hydroxymethyl-1-methylpyrazole,
4,5-diamino-1-ethyl-3-hydroxymethylpyrazole,
4,5-diamino-3-hydroxymethyl-1-isopropylpyrazole,
4,5-diamino-3-hydroxymethyl-1-tert-butylpyrazole,
4,5-diamino-3-hydroxymethyl-1-phenylpyrazole,
4,5-diamino-3-hydroxymethyl-1-(2'-methoxyphenyl) pyrazole,
4,5-diamino-3-hydroxymethyl-1-(3'-methoxyphenyl) pyrazole,
4,5-diamino-3-hydroxymethyl-1-(4'-methoxyphenyl) pyrazole,
1-benzyl-4,5-diamino-3-hydroxymethylpyrazole,
4,5-diamino-3-methyl-1-(2'-methoxyphenyl)pyrazole,
4,5-diamino-3-methyl-1-(3'-methoxyphenyl)pyrazole,
4,5-diamino-3-methyl-1-(4'-methoxyphenyl)pyrazole,
3-aminomethyl-4,5-diamino-1-methylpyrazole,
3-aminomethyl-4,5-diamino-1-ethylpyrazole,
3-aminomethyl-4,5-diamino-1-isopropylpyrazole,
3-aminomethyl-4,5-diamino-1-tert-butylpyrazole,
4,5-diamino-3-dimethylaminomethyl-1-methylpyrazole,
4,5-diamino-3-dimethylaminomethyl-1-isopropylpyrazole,
4,5-diamino-3-dimethylaminomethyl-1-tert-butylpyrazole,
4,5-diamino-3-ethylaminomethyl-1-methylpyrazole,
4,5-diamino-3-ethylaminomethyl-1-ethylpyrazole,
4,5-diamino-3-ethylaminomethyl-1-isopropylpyrazole,
4,5-diamino-3-ethylaminomethyl-1-tert-butylpyrazole,
4,5-diamino-3-methylaminomethyl-1-methylpyrazole,
4,5-diamino-3-methylaminomethyl-1-isopropylpyrazole,
4,5-diamino-1-ethyl-3-methylaminomethylpyrazole,
1-tert-butyl-4,5-diamino-3-methylaminomethylpyrazole,
4,5-diamino-3-{(β-hydroxyethyl)aminomethyl}-1-methylpyrazole,
4,5-diamino-3-{(β-hydroxyethyl)aminomethyl}-1-isopropylpyrazole,
4,5-diamino-1-ethyl-3-{(β-hydroxyethyl)aminomethyl}pyrazole,
1-tert-butyl-4,5-diamino-3-{(β-hydroxyethyl)aminomethyl}pyrazole,
4-amino-5-(β-hydroxyethyl)amino-1,3-dimethylpyrazole,
4-amino-5-(β-hydroxyethyl)amino-1-isopropyl-3-methylpyrazole,
4-amino-5-(β-hydroxyethyl)amino-1-ethyl-3-methylpyrazole,
4-amino-5-(β-hydroxyethyl)amino-1-tert-butyl-3-methylpyrazole,
4-amino-5-(β-hydroxyethyl)amino-1-phenyl-3-methylpyrazole,
4-amino-5-(β-hydroxyethyl)amino-1-(2-methoxyphenyl)-3-methylpyrazole,
4-amino-5-(β-hydroxyethyl)amino-1-(3-methoxyphenyl)-3-methylpyrazole,
4-amino-5-(β-hydroxyethyl)amino-1-(4-methoxyphenyl)-3-methylpyrazole,
4-amino-5-(β-hydroxyethyl)amino-1-benzyl-3-methylpyrazole,
4-amino-1-ethyl-3-methyl-5-methylaminopyrazole,
4-amino-1-tert-butyl-3-methyl-5-methylaminopyrazole,
4,5-diamino-1,3-dimethylpyrazole,
4,5-diamino-3-tert-butyl-1-methylpyrazole,
4,5-diamino-1-tert-butyl-3-methylpyrazole,
4,5-diamino-1-methyl-3-phenylpyrazole,
4,5-diamino-1-(β-hydroxyethyl)-3-methylpyrazole,
4,5-diamino-1-(β-hydroxyethyl)-3-phenylpyrazole,
4,5-diamino-1-methyl-3-(2'-chlorophenyl)pyrazole,
4,5-diamino-1-methyl-3-(4'-chlorophenyl)pyrazole,
4,5-diamino-1-methyl-3-(3'-trifluoromethylphenyl) pyrazole,
4,5-diamino-1,3-diphenylpyrazole,
4,5-diamino-3-methyl-1-phenylpyrazole,
4-amino-1,3-dimethyl-5-phenylaminopyrazole,
4-amino-1-ethyl-3-methyl-5-phenylaminopyrazole,
4-amino-1,3-dimethyl-5-methylaminopyrazole,
4-amino-3-methyl-1-isopropyl-5-methylaminopyrazole,
4-amino-3-isobutoxymethyl-1-methyl-5-methylaminopyrazole,
4-amino-3-methoxyethoxymethyl-1-methyl-5-methylaminopyrazole,
4-amino-3-hydroxymethyl-1-methyl-5-methylaminopyrazole,
4-amino-1,3-diphenyl-5-phenylaminopyrazole,
4-amino-3-methyl-5-methylamino-1-phenylpyrazole,
4-amino-1,3-dimethyl-5-hydrazinopyrazole,
5-amino-3-methyl-4-methylamino-1-phenylpyrazole,
5-amino-1-methyl-4-(N,N-methylphenyl)amino-3-(4'-chlorophenyl)pyrazole,
5-amino-3-ethyl-1-methyl-4-(N,N-methylphenyl)aminopyrazole,
5-amino-1-methyl-4-(N,N-methylphenyl)amino-3-phenylpyrazole,
5-amino-3-ethyl-4-(N,N-methylphenyl)aminopyrazole,
5-amino-4-(N,N-methylphenyl)amino-3-phenylpyrazole,
5-amino-4-(N,N-methylphenyl)amino-3-(4'-methylphenyl)pyrazole,
5-amino-3-(4'-chlorophenyl)-4-(N,N-methylphenyl)aminopyrazole,
5-amino-3-(4'-methoxyphenyl)-4-(N,N-methylphenyl)aminopyrazole,
4-amino-5-methylamino-3-phenylpyrazole,
4-amino-5-ethylamino-3-phenylpyrazole,
4-amino-5-ethylamino-3-(4'-methylphenyl)pyrazole,
4-amino-3-phenyl-5-propylaminopyrazole,
4-amino-5-butylamino-3-phenylpyrazole,
4-amino-3-phenyl-5-phenylaminopyrazole,
4-amino-5-benzylamino-3-phenylpyrazole,
4-amino-5-(4'-chlorophenyl)amino-3-phenylpyrazole,
4-amino-3-(4'-chlorophenyl)-5-phenylaminopyrazole,
4-amino-3-(4'-methoxyphenyl)-5-phenylaminopyrazole,
1-(4'-chlorobenzyl)-4,5-diamino-3-methylpyrazole, 4,5-diamino-3-hydroxymethyl-1-isopropylpyrazole,
4-amino-1-ethyl-3-methyl-5-methylaminopyrazole,
4-amino-5-(2'-aminoethyl)amino-1,3-dimethylpyrazole, and acid addition salts thereof.

38. A composition according to claim 37, wherein said diaminopyrazoles of formula (III) are chosen from:
4,5-diamino-1,3-dimethylpyrazole,
4,5-diamino-3-methyl-1-phenylpyrazole,
4,5-diamino-1-methyl-3-phenylpyrazole,
4-amino-1,3-dimethyl-5-hydrazinopyrazole,
1-benzyl-4,5-diamino-3-methylpyrazole,
4,5-diamino-3-tert-butyl-1-methylpyrazole,
4,5-diamino-1-tert-butyl-3-methylpyrazole,
4,5-diamino-1-(β-hydroxyethyl)-3-methylpyrazole,
4,5-diamino-1-ethyl-3-methylpyrazole,
4,5-diamino-1-ethyl-3-(4'-methoxyphenyl)pyrazole,
4,5-diamino-1-ethyl-3-hydroxymethylpyrazole,
4,5-diamino-3-hydroxymethyl-1-methylpyrazole,
4,5-diamino-3-hydroxymethyl-1-isopropylpyrazole,
4,5-diamino-3-methyl-1-isopropylpyrazole,
4-amino-5-(2'-aminoethyl)amino-1,3-dimethylpyrazole, and acid addition salts thereof.

39. A composition according to claim 33, wherein said triaminopyrazoles are chosen from compounds of formula (IV), and acid addition salts thereof:

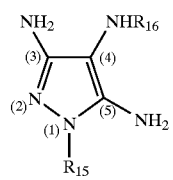

(IV)

in which:
R$_{15}$ and R$_{16}$, which are identical or different, are chosen from a hydrogen atom, a C$_1$–C$_4$ alkyl and a C$_2$–C$_4$ hydroxyalkyl radical.

40. A composition according to claim 39 wherein said triaminopyrazoles of formula (IV) are chosen from 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and acid addition salts thereof.

41. A composition according to claim 33, wherein R$_1$ is chosen from a halogen atom, a C$_1$–C$_4$ alkyl radical, a C$_1$–C$_4$ monohydroxyalkyl radical, a C$_2$–C$_4$ polyhydroxyalkyl radical, a C$_1$–C$_4$ alkoxy radical, a C$_1$–C$_4$ monohydroxyalkoxy radical and a C$_2$–C$_4$ polyhydroxyalkoxy radical.

42. A composition according to claim 33, wherein R$_1$ is chosen from a C$_1$–C$_4$ alkyl radical.

43. A composition according to claim 33, wherein the at least one coupler is chosen from 3-amino-2-chloro-6-methylphenol and acid addition salts thereof.

44. A composition according to claim 33, wherein the at least one oxidation base is chosen from diaminopyrazoles of formula (II), and acid addition salts thereof:

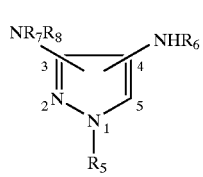

(II)

in which:
R$_5$ is chosen from a C$_2$–C$_4$ hydroxyalkyl radical;
R$_6$ and R$_7$ which are identical or different, are chosen from a hydrogen atom, a C$_1$–C$_4$ alkyl radical, a C$_2$–C$_4$ hydroxyalkyl radical, a benzyl radical and a phenyl radical; and
R$_8$ is chosen from a hydrogen atom, a C$_1$–C$_6$ alkyl radical and a C$_2$–C$_4$ hydroxyalkyl radical.

45. A composition according to claim 33, wherein said composition is in a medium suitable for dyeing.

46. A composition according to claim 33, wherein said at least one oxidation base is present in an amount ranging from 0.0005 to 12% by weight relative to the total weight of the composition.

47. A composition according to claim 46, wherein said at least one oxidation base is present in an amount ranging from 0.005 to 6% by weight relative to the total weight of the composition.

48. A composition according to claim 33, wherein said at least one coupler is present in an amount ranging from 0.0001 to 5% by weight relative to the total weight of the composition.

49. A composition according to claim 48, wherein said at least one coupler is present in an amount ranging from 0.005 to 3% by weight relative to the total weight of the composition.

50. A composition according to claim 33, wherein said acid addition salts are chosen from hydrochlorides, hydrobromides, sulphates, tartrates, lactates and acetates.

51. A composition according to claim 45, wherein said medium suitable for dyeing or support comprises water or a mixture of water and at least one organic solvent.

52. A composition according to claim 51, wherein said at least one organic solvent is chosen from C$_1$–C$_4$ lower alkanols, glycerol, glycols and glycol ethers, and aromatic alcohols.

53. A composition according to claim 33, wherein said composition has a pH ranging from 3 to 12.

54. A composition according to claim 33, wherein said composition is in the form of a liquid, a cream, or a gel.

55. A composition according to claim 33, wherein said composition is in the form of a liquid, a cream, a gel, or in any other form suitable for dyeing human hair.

* * * * *

UNITED STATES PATENT AND TRADEMARK OFFICE
CERTIFICATE OF CORRECTION

PATENT NO. : 6,780,203 B1
DATED : August 24, 2004
INVENTOR(S) : Mireille Maubru et al.

It is certified that error appears in the above-identified patent and that said Letters Patent is hereby corrected as shown below:

Column 12,
Line 42, before "at least" delete "and".

Column 14,
Line 54, delete the second occurrence of "$R_1$ is chosen from".

Column 15,
Line 58, "from $R_1$ is chosen from a" should read -- from a --.

Column 19,
Line 6, "4,5-diamino-3-(4'-methoxyphenyl)1-isopropylpyrazole," should read
-- 4,5-diamino-3-(4'-methoxyphenyl)-1-isopropylpyrazole, --

Signed and Sealed this

Sixteenth Day of November, 2004

JON W. DUDAS
*Director of the United States Patent and Trademark Office*